US009709521B2

(12) United States Patent
Matzinger et al.

(10) Patent No.: US 9,709,521 B2
(45) Date of Patent: Jul. 18, 2017

(54) SYSTEM AND METHOD FOR MEASURING AN ANALYTE IN A SAMPLE AND CORRECTING FOR INTERFERENTS

(75) Inventors: David Matzinger, Menlo Park, CA (US); Maria Teodorczyk, San Jose, CA (US)

(73) Assignee: Cilag GmbH International, Zug (CH)

( * ) Notice: Subject to any disclaimer, the term of this patent is extended or adjusted under 35 U.S.C. 154(b) by 769 days.

(21) Appl. No.: 14/007,234

(22) PCT Filed: Mar. 20, 2012

(86) PCT No.: PCT/US2012/029821
§ 371 (c)(1),
(2), (4) Date: Oct. 31, 2013

(87) PCT Pub. No.: WO2012/134890
PCT Pub. Date: Oct. 4, 2012

(65) Prior Publication Data
US 2014/0311924 A1    Oct. 23, 2014

Related U.S. Application Data

(60) Provisional application No. 61/467,719, filed on Mar. 25, 2011.

(51) Int. Cl.
G01F 1/64    (2006.01)
G01N 27/26    (2006.01)
G01N 27/327    (2006.01)
A61B 5/145    (2006.01)

(52) U.S. Cl.
CPC ...... G01N 27/3274 (2013.01); A61B 5/14532 (2013.01); A61B 2562/0295 (2013.01)

(58) Field of Classification Search
CPC ............ A61B 5/150114; A61B 5/1411; A61B 5/14546; A61B 5/14552; A61B 5/157; A61B 5/6826; A61B 5/6838
USPC .......................................................... 422/410
See application file for complete search history.

(56) References Cited

U.S. PATENT DOCUMENTS

2006/0074564 A1    4/2006  Bartkowiak et al.
2006/0240540 A1*  10/2006  Nakatsuka ......... G01N 27/3274
                                                                       435/287.2
2009/0157344 A1    6/2009  Burke et al.
2009/0322341 A1   12/2009  Kraft et al.
(Continued)

OTHER PUBLICATIONS

International Application No. PCT/US2012/029821, International Preliminary Report and Written Opinion dated Oct. 10, 2013, 11 pages, International Searching Authority.

Primary Examiner — Jill Warden
Assistant Examiner — Brittany Fisher

(57) ABSTRACT

Methods and systems to apply a plurality of test voltages to the test strip and measure a current transient output resulting from an electrochemical reaction in a test chamber of the test strip so that a glucose concentration can be determined that account for interferent substances in the body fluid sample. A method of determining blood glucose concentration with a glucose measurement system that includes a test strip and test meter. The test meter has a microcontroller configured to apply a plurality of test voltages to the test strip and measure a current transient output resulting from an electrochemical reaction in a test chamber of the test strip.

17 Claims, 16 Drawing Sheets

(56) References Cited

U.S. PATENT DOCUMENTS

2011/0005941 A1 1/2011 Blythe et al.
2011/0073494 A1 3/2011 McColl et al.

* cited by examiner

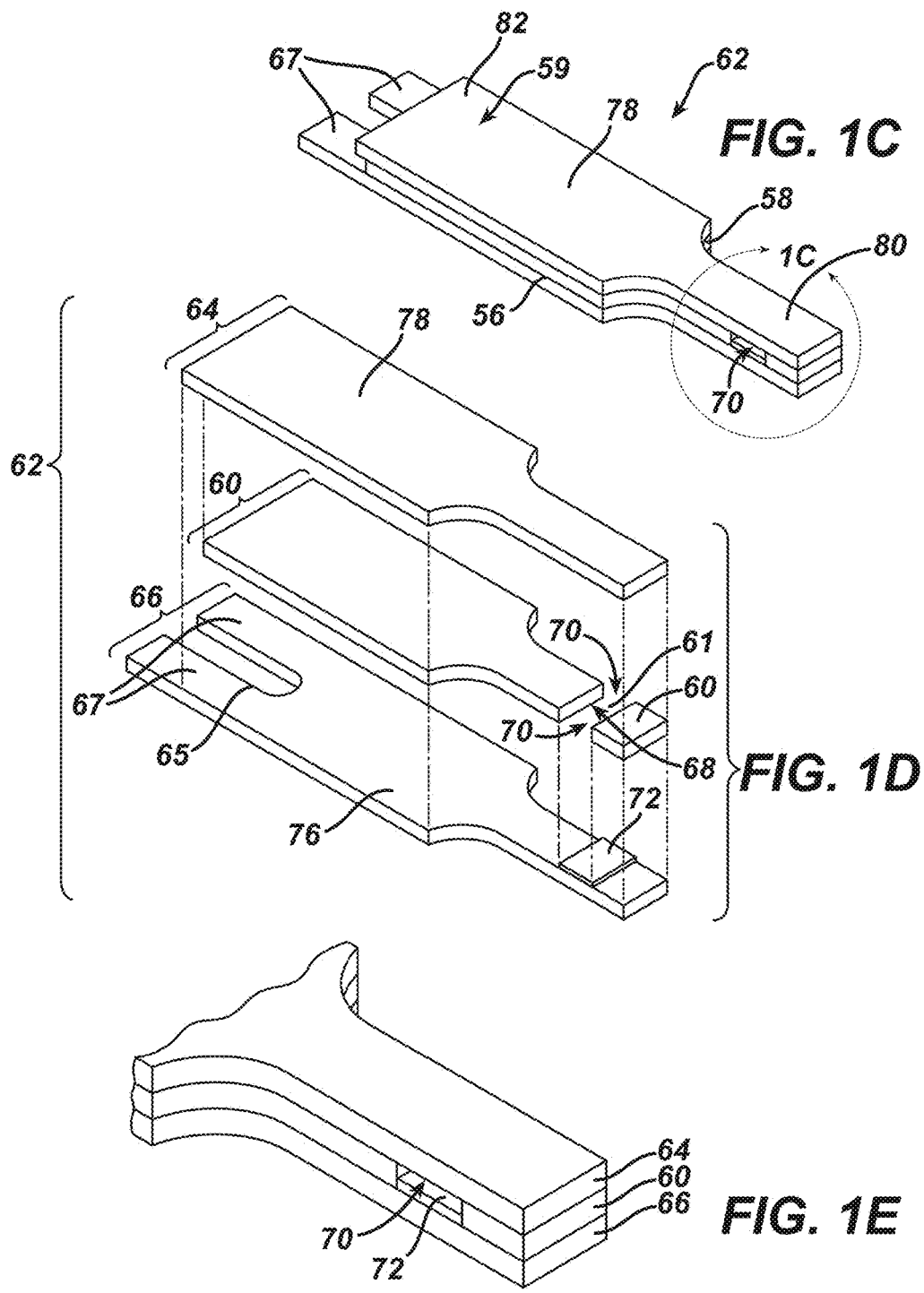

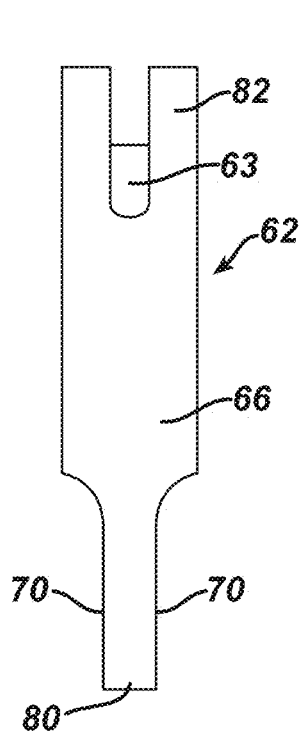 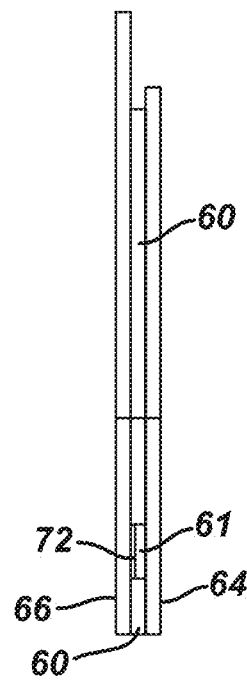 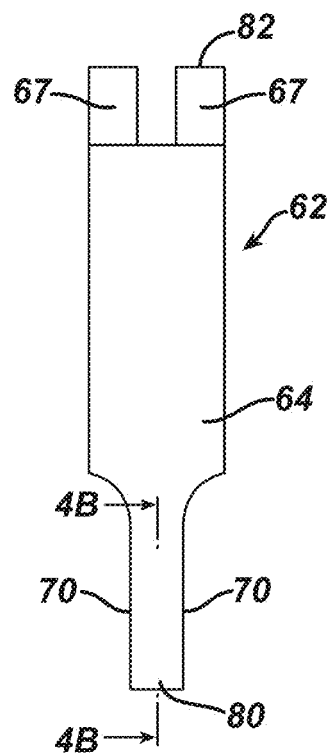
FIG. 2   FIG. 3   FIG. 4A
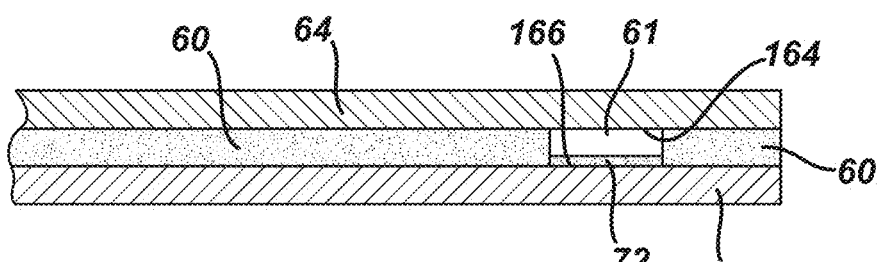
FIG. 4B

SYSTEM AND METHOD FOR MEASURING AN ANALYTE IN A SAMPLE AND CORRECTING FOR INTERFERENTS

PRIORITY

This application claims the benefits of priority under 35 USC§§119, 120, 365 and 371 from prior International Patent Application S.N. PCT/US12/29821 filed on Mar. 20, 2012, which claims priority from Provisional Patent Application Ser. No. 61/467,719 filed on Mar. 25, 2011, all of the prior applications are hereby incorporated by reference as if fully set forth in this application.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency and/or error. For example, interferents such as reducing agents in the form of uric acid may affect the results of the method.

SUMMARY OF THE DISCLOSURE

Applicants have discovered a technique to correct a calculated glucose concentration to filter out or account for the effects of interferents in the form of certain reducing agents such that the corrected values are at least 97% within 10%, 15%, or 20% absolute bias to reference YSI values.

Various aspects of a method of calculating an analyte concentration of a sample are provided. In one aspect, a method of determining blood glucose concentration with a glucose measurement system that includes a test strip and test meter. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; causing a transformation of analytes in the sample from one form to a different form; switching the first voltage to a second voltage different than the first voltage; changing the second voltage to a third voltage different from the second voltage; measuring a second current output of the current transient from the electrodes after the changing from the second voltage to the third voltage; estimating approximate steady state current output of the current transient after the third voltage is maintained at the electrodes; calculating a blood glucose concentration based on the first, second and third current output of the current transient with an equation of the form:

$$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right) i_r$$

where:
a, b, c, p, zgr comprise manufacturing parameters;
$i_{4.1}$ comprises the current measured at about 4.1 seconds after initiation of test sequence;
$i_5$ comprises the current measured at about 5 seconds after initiation of test sequence;
$i_{1.1}$ comprises the current measured at about 1.1 seconds after initiation of test sequence; and
correcting the blood glucose concentration with an equation of the form:

$$G_{corr} = G_1 * (A + B * i_{1.1})$$

where $G_{corr}$ comprises a corrected blood glucose concentration and coefficients A and B comprise empirically derived coefficients.

In another aspect, a method of determining blood glucose concentration with a glucose measurement system that includes a test strip and test meter is provided. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; causing a transformation of analytes in the sample from one form to a different form; switching the first voltage to a second voltage different than the first voltage; changing the second voltage to a third voltage different from the second voltage; measuring a second current output of the current transient from the electrodes after the changing from the second voltage to the third voltage; estimating approximate steady state current output of the current transient after the third voltage is maintained at the electrodes; calculating a blood glucose concentration based on the first, second and third current output of the current transient with an equation of the form:

$$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left( \frac{|i_{4.1}| + b|i_5| - c|i_{1.1}|}{|i_{4.1}| + b|i_5|} \right) i_r$$

where:
a, b, c, p, zgr comprise manufacturing parameters;
$i_{4.1}$ comprises the current measured at about 4.1 seconds after initiation of test sequence;
$i_5$ comprises the current measured at about 5 seconds after initiation of test sequence;
$i_{1.1}$ comprises the current measured at about 1.1 seconds after initiation of test sequence; and
correcting the blood glucose concentration with an equation of the form:

$$G_{corr} = G_1 * (C + D*i_{1.1} + E*(i_{1.1})^2)$$

where $G_{corr}$ comprises a corrected blood glucose concentration and coefficients C, D and E comprise empirically derived coefficients.

In yet a further embodiment, a method of determining blood glucose concentration with a glucose measurement system that includes a test strip and test meter is provided. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; causing a transformation of analytes in the sample from one form to a different form; switching the first voltage to a second voltage different than the first voltage; changing the second voltage to a third voltage different from the second voltage; measuring a second current output of the current transient from the electrodes after the changing from the second voltage to the third voltage; estimating approximate steady state current output of the current transient after the third voltage is maintained at the electrodes; calculating a blood glucose concentration based on the first, second and third current output of the current transient; deriving a first corrected blood glucose concentration; deriving a second corrected blood glucose concentration; and annunciating an error if the first and second corrected blood glucose concentration are different by more than threshold percentage. The third voltage may be different in the magnitude of the electromotive force, in polarity, or combinations of both. The deriving of the first corrected glucose concentration includes calculating with equations of the form:

$$G_1 = \left( \frac{|i_r|}{|i_l|} \right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left( \frac{|i_{4.1}| + b|i_5| - c|i_{1.1}|}{|i_{4.1}| + b|i_5|} \right) i_r$$

where:
a, b, c, p, zgr comprise manufacturing parameters;
$i_{4.1}$ comprises the current measured at about 4.1 seconds after initiation of test sequence;
$i_5$ comprises the current measured at about 5 seconds after initiation of test sequence;
$i_{1.1}$ comprises the current measured at about 1.1 seconds after initiation of test sequence; and $$G_{corr1} = G_1 * (A + B*i_{1.1})$$

where $G_{corr1}$ comprises a first corrected blood glucose concentration and coefficients A and B are empirically derived coefficients.

The aforementioned method includes deriving the second corrected glucose concentration by calculating with equations of the form $$G_1 = \left( \frac{|i_r|}{|i_l|} \right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left( \frac{|i_{4.1}| + b|i_5| - c|i_{1.1}|}{|i_{4.1}| + b|i_5|} \right) i_r$$

where:
a, b, c, p, zgr comprise manufacturing parameters;
$i_{4.1}$ comprises the current measured at about 4.1 seconds after initiation of test sequence;
$i_5$ comprises the current measured at about 5 seconds after initiation of test sequence;
$i_{1.1}$ comprises the current measured at about 1.1 seconds after initiation of test sequence; and
correcting the blood glucose concentration with an equation of the form:

$$G_{corr2} = G_1 * (C + D*i_{1.1} + E*(i1.1)^2)$$

where $G_{corr2}$ comprises a corrected blood glucose concentration and coefficients C, D and E comprise empirically derived coefficients.

In the aforementioned method, the measuring of the first current output may include measuring a current output of the at least two electrodes at about 1.1 seconds after initiation of test sequence. The measuring of the second current output may include measuring a current output of the at least two electrodes at about 4.1 seconds after initiation of test sequence. The estimating of the steady state current output may include measuring a current output of the at least two electrodes at about 5 seconds after initiation of test sequence.

In the aforementioned method, the coefficients A and B may include approximately 1.004 and approximately 0.0077, respectively. The coefficients A, B, C, D, and E may include approximately 1.004, approximately 0.0077, approximately 0.889, approximately 0.0220 and approximately −0.00036, respectively. In the aforementioned method, the coefficients A and B may include approximately 1.004 and approximately 0.0077, respectively. The coefficients C, D, and E may include approximately 0.889, approximately 0.0220 and approximately −0.00036, respectively. The sampling interval may be at approximately 50 milliseconds interval. And the manufacturing parameters a, b, c, p, zgr are such that a is approximately 0.192, b is approximately 0.68, p is approximately 0.52 and zgr is approximately 2.

In another aspect, a blood glucose measurement system is provided that includes an analyte test strip and an analyte meter. The analyte test strip includes a substrate having a reagent disposed thereon with at least two electrodes proximate the reagent in test chamber. The analyte meter includes a strip port connector disposed to connect to the two electrodes, a power supply, and a microcontroller electrically coupled to the strip port connector and the power supply. The microcontroller is programmed to determine a glucose concentration $G_1$ and a corrected glucose concentration $G_{corr}$ so that at least 97% of corrected test results are within respective bias criterion of ±10 mg/dL at 65 mg/dL, 240 mg/dL, or 450 mg/dL; ±12 mg/dL at 65 mg/dL, 240 mg/dL, or 450 mg/dL; and ±15 mg/dL at 65 mg/dL, 240 mg/dL, or 450 mg/dL to referential values, the glucose concentration and the corrected glucose concentration being derived from the following equations:

$$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right) i_r$$

where:
a, b, c, p, zgr comprise manufacturing parameters;
$i_{4.1}$ comprises the current measured at about 4.1 seconds after initiation of test sequence;
$i_5$ comprises the current measured at about 5 seconds after initiation of test sequence;
$i_{1.1}$ comprises the current measured at about 1.1 seconds after initiation of test sequence; and $$G_{corr} = G_1 * (C + D * i_{1.1} + E * (i1.1)^2)$$

where $G_{corr}$ comprises a corrected blood glucose concentration and coefficients C, D and E are empirically derived coefficients.

In the aforementioned system, the manufacturing parameters a, b, c, p, zgr are such that a comprises approximately 0.192, b comprises approximately 0.68, c comprises approximately 2, p comprises approximately 0.52, and zgr comprises approximately 2, and the coefficients C, D, and E may include approximately 0.889, approximately 0.0220 and approximately minus (−) 0.00036, respectively.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 1C illustrates a perspective view of an assembled test strip suitable for use in the system and methods disclosed herein;

FIG. 1D illustrates an exploded perspective view of an unassembled test strip suitable for use in the system and methods disclosed herein;

FIG. 1E illustrates an expanded perspective view of a proximal portion of the test strip suitable for use in the system and methods disclosed herein;

FIG. 2 is a bottom plan view of one embodiment of a test strip disclosed herein;

FIG. 3 is a side plan view of the test strip of FIG. 2;

FIG. 4A is a top plan view of the test strip of FIG. 3;

FIG. 4B is a partial side view of a proximal portion of the test strip of FIG. 4A;

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1A:
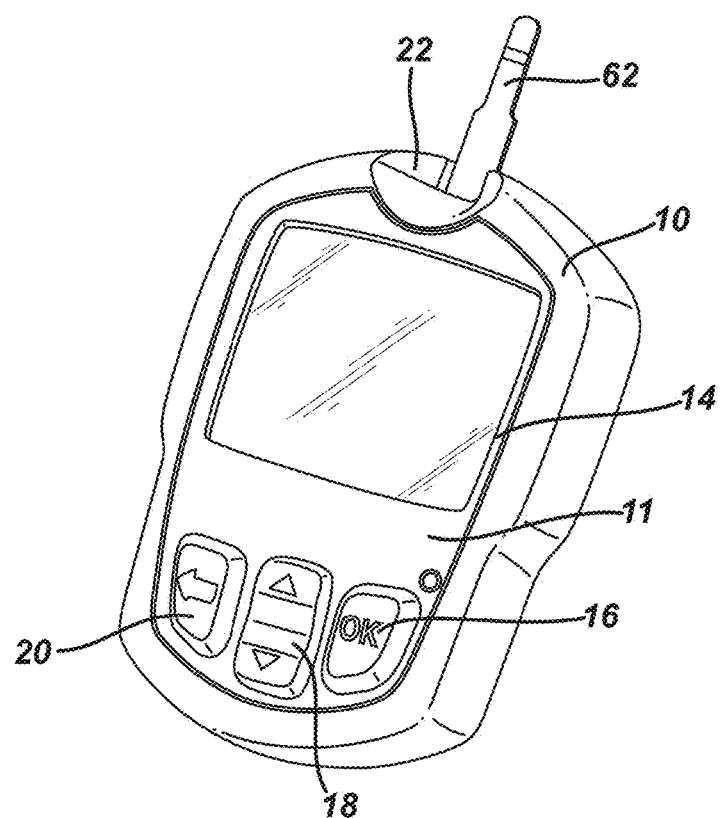
FIG. 1A illustrates a preferred blood glucose measurement system.

FIG. 1A illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1A, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, and/or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 1B:
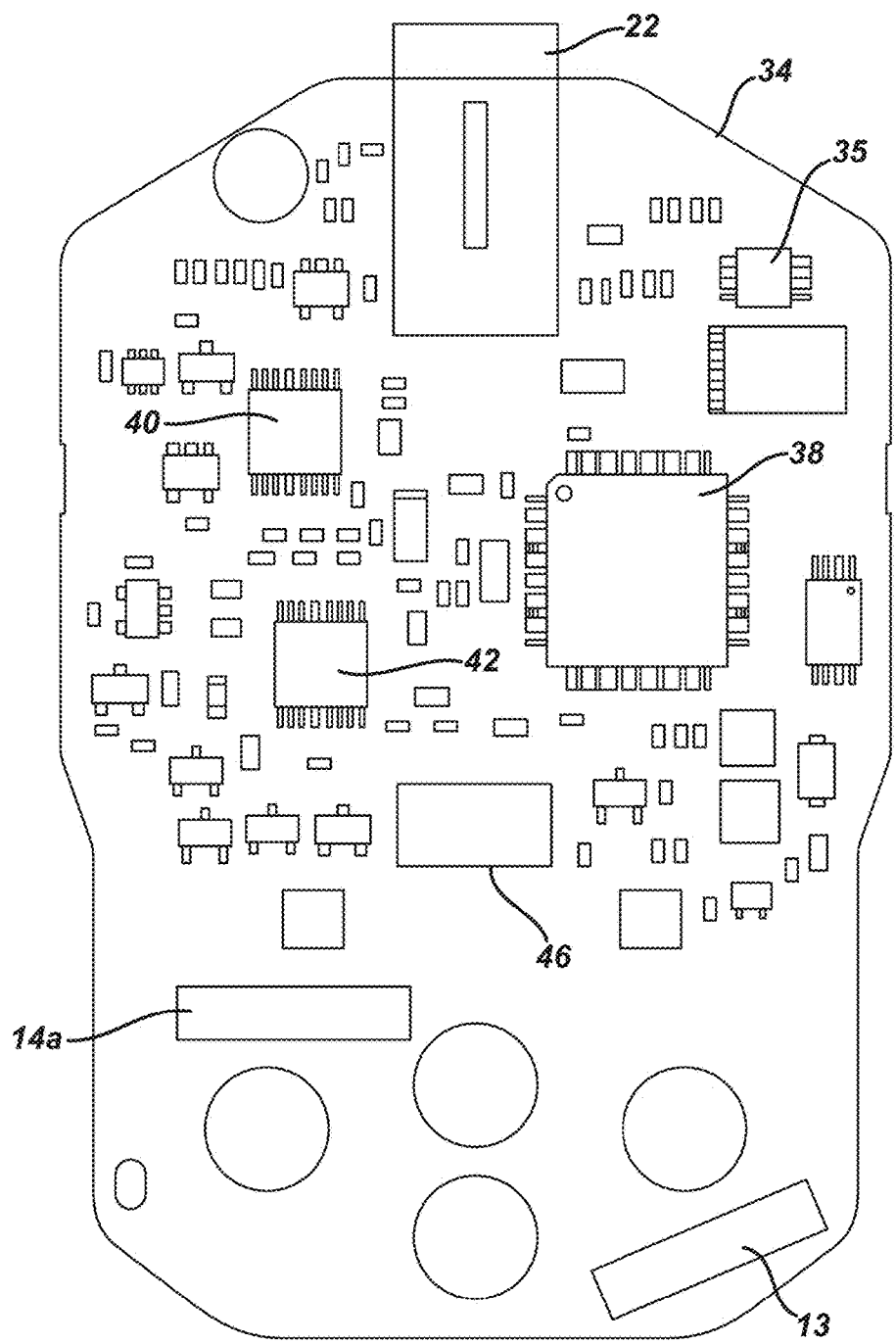
FIG. 1B illustrates the various components disposed in the meter of FIG. 1A.

FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

FIGS. 1C-1E, 2, 3, and 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1C. As shown in FIG. 1D, the test strip 62 also includes a first electrode layer 66, a second electrode layer 64, and a spacer 60 sandwiched in between the two electrode layers 64 and 66. The first electrode layer 66 may include a first electrode 66, a first connection track 76, and a first contact pad 67, where the first connection track 76 electrically connects the first electrode 66 to the first contact pad 67, as shown in FIGS. 1D and 4B. Note that the first electrode 66 is a portion of the first electrode layer 66 that is immediately underneath the reagent layer 72, as indicated by FIGS. 1D and 4B. Similarly, the second electrode layer 64 may include a second electrode 64, a second connection track 78, and a second contact pad 63, where the second connection track 78 electrically connects the second electrode 64 with the second contact pad 63, as shown in FIGS. 1D, 2, and 4B. Note that the second electrode 64 is a portion of the second electrode layer 64 that is above the reagent layer 72, as indicated by FIG. 4B. As used herein, the terms "electrode layer" and "electrode" are used interchangeably to refer to the general area encompassing an electrode or a specific location for the electrode.

As shown, the sample-receiving chamber 61 is defined by the first electrode 66, the second electrode 64, and the spacer 60 near the distal end 80 of the test strip 62, as shown in FIGS. 1D and 4B. The first electrode 66 and the second electrode 64 may define the bottom and the top of sample-receiving chamber 61, respectively, as illustrated in FIG. 4B. A cutout area 68 of the spacer 60 may define the sidewalls of the sample-receiving chamber 61, as illustrated in FIG. 4B. In one aspect, the sample-receiving chamber 61 may include ports 70 that provide a sample inlet and/or a vent, as shown in FIGS. 1C to 1E. For example, one of the ports may allow a fluid sample to ingress and the other port may allow air to egress.

In an exemplary embodiment, the sample-receiving chamber 61 (or test cell or test chamber) may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 cm$^2$ to about 0.2 cm$^2$, about 0.02 cm$^2$ to about 0.15 cm$^2$, or, preferably, about 0.03 cm$^2$ to about 0.08 cm$^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at first electrode 66, may diffuse to second electrode 64 to become reduced, and subsequently diffuse back to first electrode 66 to become oxidized again. Those skilled in the art will appreciate that various such volumes, areas, and/or spacing of electrodes is within the spirit and scope of the present disclosure.

In one embodiment, the first electrode layer 66 and the second electrode layer 64 may be a conductive material formed from materials such as gold, palladium, carbon, silver, platinum, tin oxide, iridium, indium, or combinations thereof (e.g., indium doped tin oxide). In addition, the electrodes may be formed by disposing a conductive material onto an insulating sheet (not shown) by a sputtering, electroless plating, or a screen-printing process. In one exemplary embodiment, the first electrode layer 66 and the second electrode layer 64 may be made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, and/or the spacer 60 are within the spirit and scope of the present disclosure.

Either the first electrode 66 or the second electrode 64 may perform the function of a working electrode depending on the magnitude and/or polarity of the applied test voltage. The working electrode may measure a limiting test current that is proportional to the reduced mediator concentration. For example, if the current limiting species is a reduced mediator (e.g., ferrocyanide), then it may be oxidized at the first electrode 66 as long as the test voltage is sufficiently greater than the redox mediator potential with respect to the second electrode 64. In such a situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term "bulk solution" refers to a portion of the solution sufficiently far away from the working electrode where the reduced mediator is not located within a depletion zone. It should be noted that unless otherwise stated for test strip 62, all potentials applied by test meter 10 will hereinafter be stated with respect to second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into a sample-receiving chamber 61 via a port 70. In one aspect, the port 70 and/or the sample-receiving chamber 61 may be configured such that capillary action causes the fluid sample to fill the sample-receiving chamber 61. The first electrode 66 and/or second electrode 64 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode and/or the second electrode.

In the analysis of strip 62 above, reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by GDH$_{(ox)}$ and in the process converts GDH$_{(ox)}$ to GDH$_{(red)}$, as shown in the chemical transformation T.1 below. Note that GDH$_{(ox)}$ refers to the oxidized state of GDH, and GDH$_{(red)}$ refers to the reduced state of GDH.

$$\text{D-Glucose} + \text{GDH}_{(ox)} \rightarrow \text{Gluconic acid} + \text{GDH}_{(red)} \qquad \text{T.1}$$

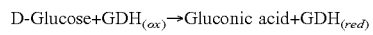

Next, GDH$_{(red)}$ is regenerated back to its active oxidized state by ferricyanide (i.e. oxidized mediator or Fe(CN)$_6^{3-}$) as shown in chemical transformation T.2 below. In the process of regenerating GDH$_{(ox)}$, ferrocyanide (i.e. reduced mediator or Fe(CN)$_6^{4-}$) is generated from the reaction as shown in T.2:

$$\text{GDH}_{(red)} + 2\text{Fe(CN)}_6^{3-} \rightarrow \text{GDH}_{(ox)} + 2\text{Fe(CN)}_6^{4-} \qquad \text{T.2}$$

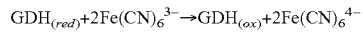

Figure 5:
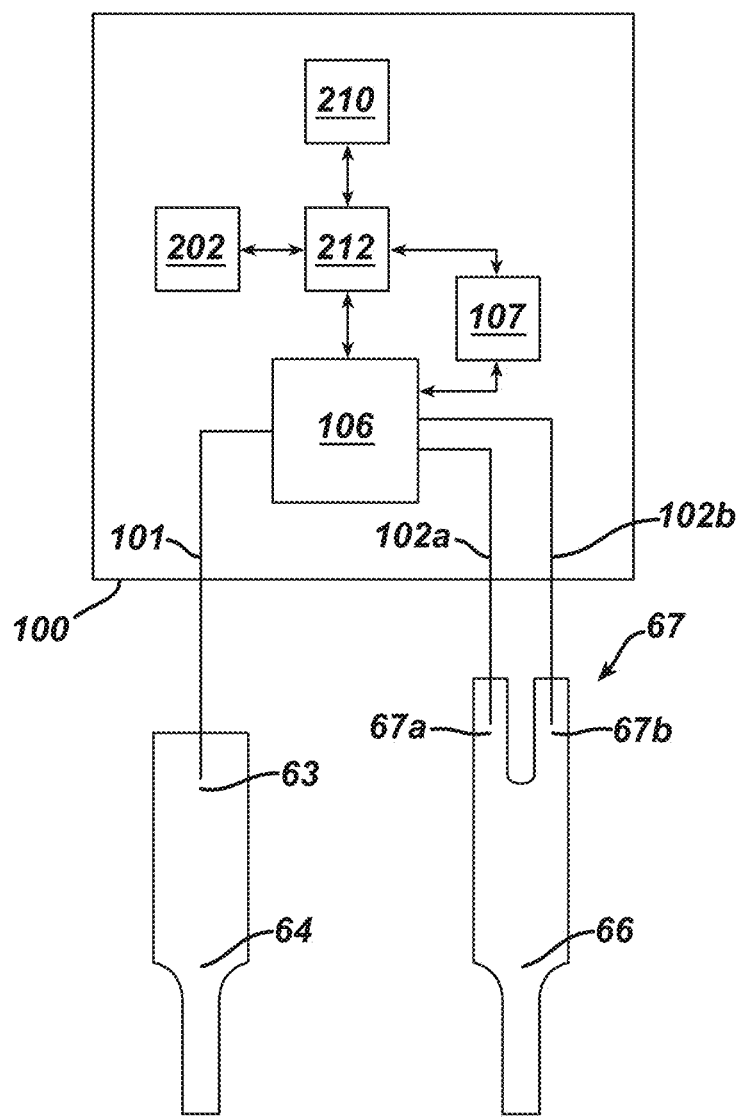
FIG. 5 is a simplified schematic showing a test meter electrically interfacing with portions of a test strip disclosed herein.

FIG. 5 provides a simplified schematic showing a test meter 100 interfacing with a first contact pad 67a, 67b and a second contact pad 63. The second contact pad 63 may be used to establish an electrical connection to the test meter through a U-shaped notch 65, as illustrated in FIG. 2. In one embodiment, the test meter 100 may include a second electrode connector 101, and a first electrode connectors (102a, 102b), a test voltage unit 106, a current measurement unit 107, a processor 212, a memory unit 210, and a visual display 202, as shown in FIG. 5. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 100 may measure the resistance or electrical continuity between the prongs 67a and 67b to determine whether the test strip 62 is electrically connected to the test meter 10.

In one embodiment, the test meter 100 may apply a test voltage and/or a current between the first contact pad 67 and the second contact pad 63. Once the test meter 100 recognizes that the strip 62 has been inserted, the test meter 100 turns on and initiates a fluid detection mode. In one embodiment, the fluid detection mode causes test meter 100 to apply a constant current of about 1 microampere between the first electrode 66 and the second electrode 64. Because the test strip 62 is initially dry, the test meter 10 measures a relatively large voltage. When the fluid sample bridges the gap between the first electrode 66 and the second electrode 64 during the dosing process, the test meter 100 will measure a decrease in measured voltage that is below a predetermined threshold causing test meter 10 to automatically initiate the glucose test.

Figure 6:
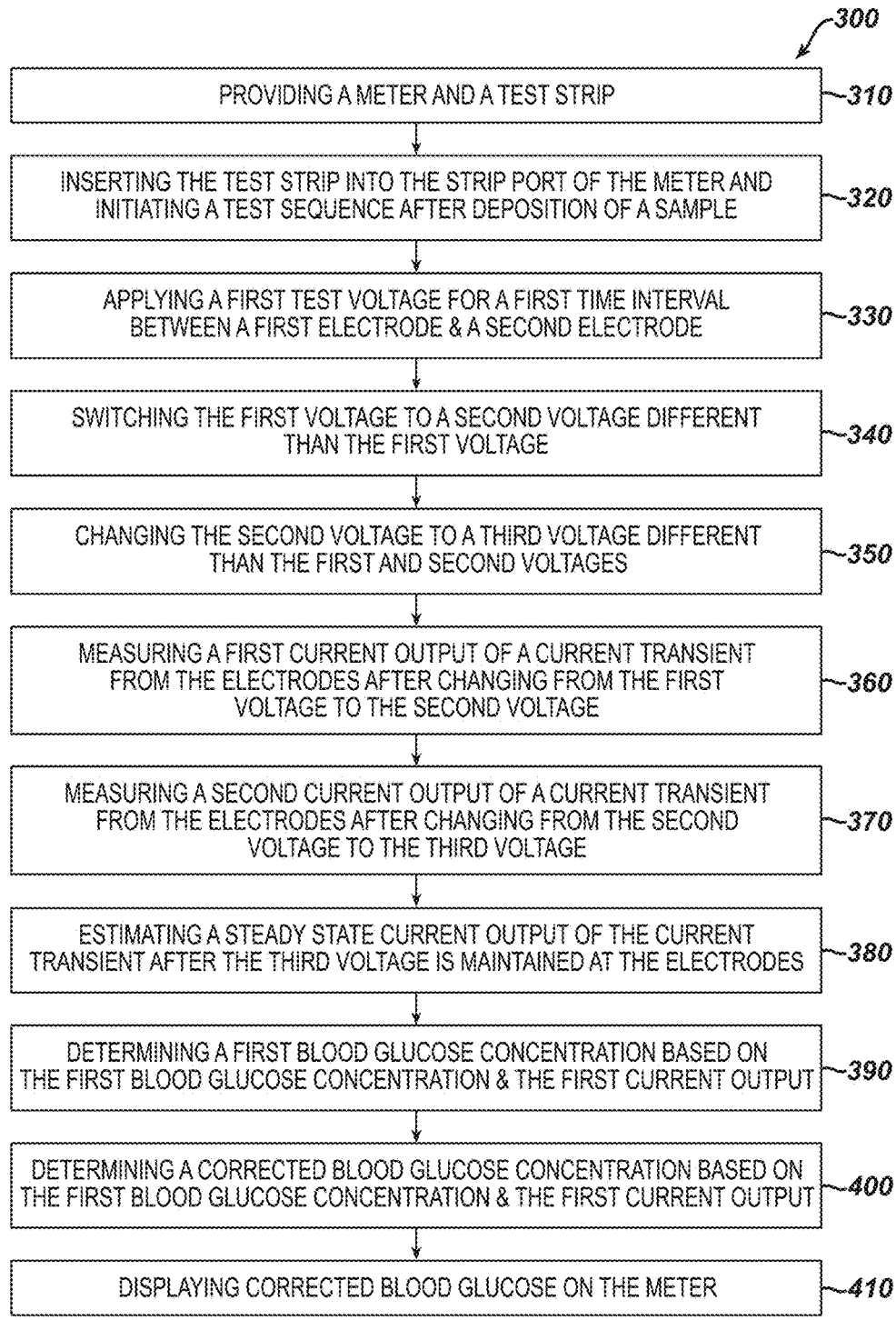
FIG. 6 is a flow diagram depicting stages in a method for determining a glucose concentration that accounts for interferent substances in the bodily fluid sample, in accordance with an embodiment of the present invention.

Referring to FIG. 6, a method 300 for determining an interferent-corrected analyte concentration (e.g., glucose) that uses the aforementioned meter 10 and test strip 62 embodiments will now be described.

In exemplary step 310, meter 10 and test strip 62 are provided. Meter 10 may include electronic circuitry that can be used to apply a plurality of voltages to the test strip 62 and to measure a current transient output resulting from an electrochemical reaction in a test chamber of the test strip 62. Meter 10 also may include a signal processor with a set of instructions for the method of determining an analyte concentration in a fluid sample as disclosed herein. In one embodiment, the analyte is blood glucose.

Figure 7A:
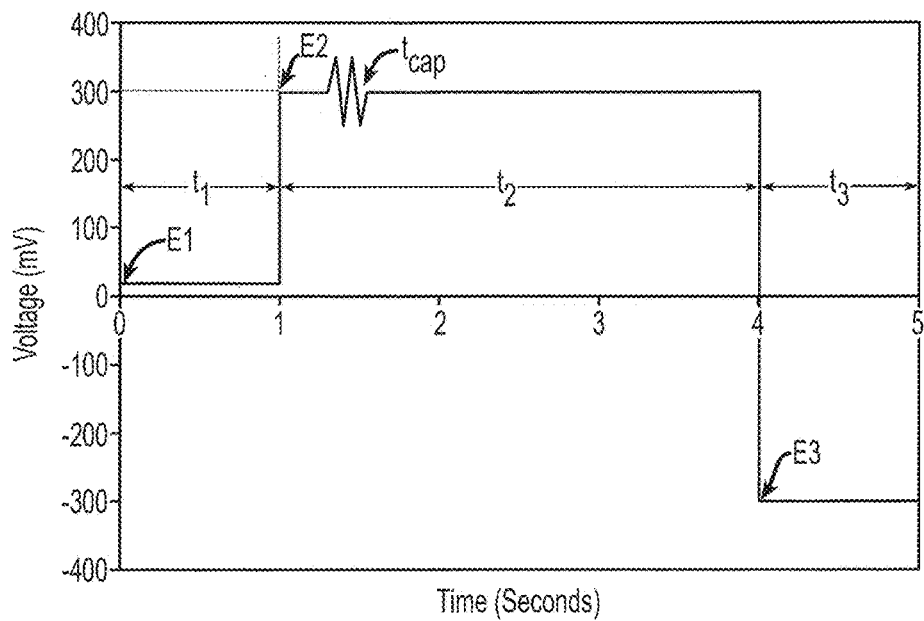
FIG. 7A shows an example of a tri-pulse potential waveform applied by the test meter of FIG. 5 to the working and counter electrodes for prescribed time intervals.

FIG. 7A is an exemplary chart of a plurality of test voltages applied to the test strip 62 for prescribed intervals. The plurality of test voltages may include a first test voltage E1 for a first time interval $t_1$, a second test voltage E2 for a second time interval $t_2$, and a third test voltage E3 for a third time interval $t_3$. The third voltage E3 may be different in the magnitude of the electromotive force, in polarity, or combinations of both with respect to the second test voltage E2. In the preferred embodiments, E3 may be of the same magnitude as E2 but opposite in polarity. A glucose test time interval $t_G$ represents an amount of time to perform the glucose test (but not necessarily all the calculations associated with the glucose test). Glucose test time interval $t_G$ may range from about 1.1 seconds to about 5 seconds. Further, as illustrated in FIG. 6A, the second test voltage E2 may include a constant (DC) test voltage component and a superimposed alternating (AC), or alternatively oscillating, test voltage component. The superimposed alternating or oscillating test voltage component may be applied for a time interval indicated by $t_{cap}$.

The plurality of test current values measured during any of the time intervals may be performed at a frequency ranging from about 1 measurement per microsecond to about one measurement per 100 milliseconds and preferably at about 50 milliseconds. While an embodiment using three test voltages in a serial manner is described, the glucose test may include different numbers of open-circuit and test voltages. For example, as an alternative embodiment, the glucose test could include an open-circuit for a first time interval, a second test voltage for a second time interval, and a third test voltage for a third time interval. It should be noted that the reference to "first," "second," and "third" are chosen for convenience and do not necessarily reflect the order in which the test voltages are applied. For instance, an embodiment may have a potential waveform where the third test voltage may be applied before the application of the first and second test voltage.

In exemplary step 320, the glucose assay is initiated by inserting a test strip 62 into the test meter 10 and by depositing a sample on the test strip 62. In exemplary step 330, the test meter 10 may apply a first test voltage E1 (e.g., approximately 20 mV in FIG. 7A) between first electrode 66 and second electrode 64 for a first time interval $t_1$ (e.g., 1 second in FIG. 7A). The first time interval $t_1$ may range from about 0.1 seconds to about 3 seconds and preferably range from about 0.2 seconds to about 2 seconds, and most preferably range from about 0.3 seconds to about 1.1 seconds.

Figure 7B:
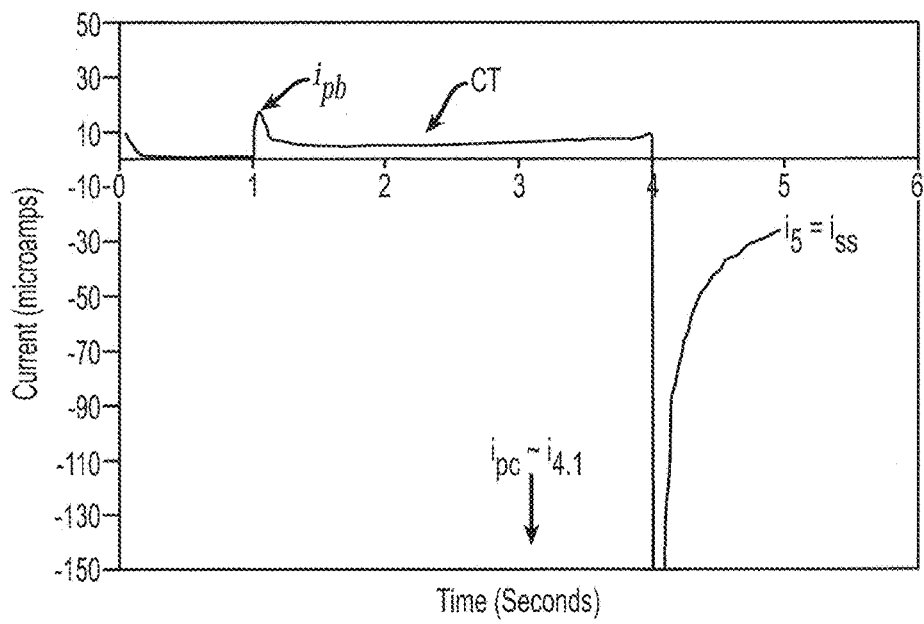
FIG. 7B shows a first and second current transient CT generated testing a physiological sample containing 62 mg/dL glucose concentration without added interferents (solid line) and with a 20 mg/dL ascorbate concentration (dotted line)

The first time interval $t_1$ may be sufficiently long so that the sample-receiving chamber 61 may fully fill with sample and also so that the reagent layer 72 may at least partially dissolve or solvate. In one aspect, the first test voltage E1 may be a value relatively close to the redox potential of the mediator so that a relatively small amount of a reduction or oxidation current is measured. FIG. 7B shows that a relatively small amount of current is observed during the first time interval $t_1$ compared to the second and third time intervals $t_2$ and $t_3$. For example, when using ferricyanide and/or ferrocyanide as the mediator, the first test voltage E1 in FIG. 7A may range from about 1 mV to about 100 mV, preferably range from about 5 mV to about 50 mV, and most preferably range from about 10 mV to about 30 mV. Although the applied voltages are given as positive values in the preferred embodiments, the same voltages in the negative domain could also be utilized to accomplish the intended purpose of the claimed invention.

In exemplary step 340, after applying the first test voltage E1, the test meter 10 applies a second test voltage E2 between first electrode 66 and second electrode 64 (e.g., approximately 300 mVolts in FIG. 7A), for a second time interval $t_2$ (e.g., about 3 seconds in FIG. 7A). The second test voltage E2 may be a value different than the first test voltage E1 and may be sufficiently negative of the mediator redox potential so that a limiting oxidation current is measured at the second electrode 64. For example, when using ferricyanide and/or ferrocyanide as the mediator, the second test voltage E2 may range from about zero mV to about 600 mV, preferably range from about 100 mV to about 600 mV, and more preferably is about 300 mV.

The second time interval $t_2$ should be sufficiently long so that the rate of generation of reduced mediator (e.g., ferrocyanide) may be monitored based on the magnitude of a limiting oxidation current. Reduced mediator is generated by enzymatic reactions with the reagent layer 72. During the second time interval $t_2$, a limiting amount of reduced mediator is oxidized at second electrode 64 and a non-limiting amount of oxidized mediator is reduced at first electrode 66 to form a concentration gradient between first electrode 66 and second electrode 64.

In an exemplary embodiment, the second time interval $t_2$ should also be sufficiently long so that a sufficient amount of ferricyanide may be diffused to the second electrode 64 or diffused from the reagent on the first electrode. A sufficient amount of ferricyanide is required at the second electrode 64 so that a limiting current may be measured for oxidizing ferrocyanide at the first electrode 66 during the third test voltage E3. The second time interval $t_2$ may be less than about 60 seconds, and preferably may range from about 1.1 seconds to about 10 seconds, and more preferably range from about 2 seconds to about 5 seconds. Likewise, the time interval indicated as $t_{cap}$, in FIG. 7A may also last over a range of times, but in one exemplary embodiment it has a duration of about 20 milliseconds. In one exemplary embodiment, the superimposed alternating test voltage component is applied after about 0.3 seconds to about 0.4 seconds after the application of the second test voltage E2, and induces a sine wave having a frequency of about 109 Hz with an amplitude of about +/−50 mV.

FIG. 7B shows a relatively small peak $i_{pb}$ after the beginning of the second time interval $t_2$ followed by a gradual increase of an absolute value of an oxidation current during the second time interval $t_2$. The small peak $i_{pb}$ occurs due oxidation of endogenous or exogenous reducing agents (e.g., uric acid) after a transition from first voltage E1 to second voltage E2. Thereafter, there is a gradual absolute decrease in oxidation current after the small peak $i_{pb}$ is caused by the generation of ferrocyanide by reagent layer 72, which then diffuses to second electrode 64.

In exemplary step 350, after applying the second test voltage E2, the test meter 10 applies a third test voltage E3 between the first electrode 66 and the second electrode 64 (e.g., about −300 mVolts in FIG. 7A) for a third time interval $t_3$ (e.g., 1 second in FIG. 7A). The third test voltage E3 may be a value sufficiently positive of the mediator redox potential so that a limiting oxidation current is measured at the first electrode 66. For example, when using ferricyanide and/or ferrocyanide as the mediator, the third test voltage E3 may range from about zero mV to about −600 mV, preferably range from about −100 mV to about −600 mV, and more preferably is about −300 mV.

The third time interval $t_3$ may be sufficiently long to monitor the diffusion of reduced mediator (e.g., ferrocyanide) near the first electrode 66 based on the magnitude of the oxidation current. During the third time interval $t_3$, a limiting amount of reduced mediator is oxidized at first electrode 66 and a non-limiting amount of oxidized mediator is reduced at the second electrode 64. The third time interval $t_3$ may range from about 0.1 seconds to about 5 seconds and preferably range from about 0.3 seconds to about 3 seconds, and more preferably range from about 0.5 seconds to about 2 seconds.

FIG. 7B shows a relatively large peak $i_{pc}$ at the beginning of the third time interval $t_3$ followed by a decrease to a steady-state current $i_{ss}$ value. In one embodiment, the second test voltage E2 may have a first polarity and the third test voltage E3 may have a second polarity that is opposite to the first polarity. In another embodiment, the second test voltage E2 may be sufficiently negative of the mediator redox potential and the third test voltage E3 may be sufficiently positive of the mediator redox potential. The third test voltage E3 may be applied immediately after the second test voltage E2. However, one skilled in the art will appreciate that the magnitude and polarity of the second and third test voltages may be chosen depending on the manner in which analyte concentration is determined.

A blood glucose concentration can be determined based on the test current values. A first glucose concentration $G_1$ may be calculated using a glucose algorithm as shown in Equation 1:

$$G_1 = \left(\frac{i_2}{i_3}\right)^p \times (a \times i_1 - z) \quad \text{Eq. 1}$$

Where
$i_1$ is a first test current value,
$i_2$ is a second test current value,
$i_3$ is a third test current value, and
the terms a, p, and z can be empirically derived calibration constants.

All test current values (e.g., $i_1$, $i_2$, and $i_3$) in Equation 1 use the absolute value of the current. The first test current value $i_1$ and the second test current value $i_2$ can each be defined by an average or summation of one or more predetermined test current values that occur during the third time interval $t_3$. The term $i_2$ is a second current value that is based on a fourth current value $i_4$, a fifth current value $i_5$, and a sixth current value $i_6$ measured during a third time interval. The third test current value $i_3$ can be defined by an average or summation of one or more predetermined test current values that occur during the second time interval $t_2$. One skilled in the art will appreciate that names "first," "second," and "third" are chosen for convenience and do not necessarily reflect the order in which the current values are calculated. A derivation of Eq. 1 can be found in U.S. Pat. No. 7,749,371, patented Jul. 6, 2010, which was filed on 30 Sep. 2005 and entitled "Method and Apparatus for Rapid Electrochemical Analysis," which is hereby incorporated by reference in its entirety into this application and attached hereto as part of the Appendix.

Referring now to FIGS. 7A and 7B, the peak current (FIG. 7B) observed at the end of $t_1$ and the beginning of the second test potential time interval $t_2$ (FIG. 7A) may be denoted as $i_{pb}$, and the peak current exhibited at the start of the third test potential time interval $t_3$ (FIG. 7A) may be denoted as $i_{pc}$. Equation 2 describes a relationship between the first current transient CT and second current transient CT when a test strip 62 is tested with a sample containing an interferent and no glucose.

$$i_{pc} - 2i_{pb} = -i_{ss} \quad \text{Eq. 2}$$

In the case where there is no glucose in the sample, it is believed that the reagent layer 72 does not generate substantial amount of reduced mediator. Therefore, the current transients would reflect only the oxidation of interferents. At the early time scale regime of around 1.0 seconds, it is assumed that reagent layer 72 does not generate a significant amount of reduced mediator because of the glucose reaction. Further, it is assumed that the reduced mediator which is generated will mostly remain near first electrode 66, where reagent layer 72 was initially deposited, and not significantly diffuse to second electrode 64. Therefore, the magnitude of $i_{pb}$ is predominantly ascribed to interferent oxidation at second electrode 64 which is a direct interferent current.

At a duration after the third voltage E3 has been provided to the strip (e.g., about −300 mV) at around 4.1 seconds, reagent layer 72 does generate a significant amount of reduced mediator at first electrode 66 in the presence of glucose because of the glucose reaction. A significant amount of reduced mediator can also be generated because of a possible oxidation of an interferent with the oxidized mediator. As mentioned earlier, interferent that reduces oxidized mediator contributes to a current which may be referred to as an indirect current. In addition, interferents can also be oxidized directly at first electrode 66 which may be referred to as a direct current. For the situation in which the mediator can be oxidized at the working electrode, it may be assumed that the sum of the direct oxidation and indirect oxidation is approximately equal to a direct oxidation current that would have been measured if there was no oxidized mediator disposed on the working electrode. In summary, the magnitude of the is ascribed to both indirect and direct interferent oxidation, and the glucose reaction at the first electrode 66. Because it has been determined that $i_{pb}$ is controlled mainly by interferents, $i_{pc}$ can be used with $i_{pb}$ together to determine a correction factor. For example, as shown below $i_{pb}$ can be used with $i_{pc}$ in a mathematical function to determine a corrected current $i_{2(Corr)}$ which is proportional to glucose and less sensitive to interferents:

$$i_{2(CORR)} = i_2 \left[\frac{|i_{pc}| - |2i_{pb}| + |i_{ss}|}{|i_{pc}| + |i_{ss}|}\right] \quad \text{Eq. 3}$$

In exemplary step 360, $i_{pb}$ is measured after the start of the second test potential time interval $t_2$. In exemplary step 370, $i_{pc}$ is measured at the start of the third test potential time interval $t_3$. $i_{pc}$ may be the test current value at about 4.1 seconds, and $i_{pb}$ may be the test current value at about 1.1 second, based on the test voltage and test current waveforms in FIGS. 7A and 7B.

Eq. 3 was empirically derived to calculate a current $i_{2(Corr)}$ which is proportional to glucose and has a relative fraction of current removed that is ascribed to interferents. The term $i_{ss}$ was added to both the numerator and denominator to allow the numerator to approach zero when no glucose is present. Determination of the steady-state current $i_{ss}$ following application of the second electric potential is detailed in co-pending patent application Ser. No. 11/278,341, which is incorporated by reference into this application herein and attached hereto as part of the appendix. Some examples of methods for calculating $i_{ss}$ can be found in U.S. Pat. Nos. 5,942,102 and 6,413,410, each of which is hereby incorporated by reference in its entirety and attached hereto as part of the Appendix.

In exemplary step 380, $i_{ss}$ is estimated by multiplying the test current value at 5 seconds with a constant $K_8$ (e.g., 0.678). Thus, $i_{ss}$ can be approximated as $i(5) \times K_8$. The term $K_8$ can be estimated using Equation 4 where the number 0.975 is about the time in seconds after the third test voltage E3 is applied that corresponds to the current at approximately 5 seconds for the particular embodiment of the strip 62, which, assuming a linear variation over the time between about 0.95 seconds and 1 second, is the average current between 0.95 and 1 second, the term D is assumed to be about $5 \times 10^{-6}$ cm$^2$/sec as a typical diffusion coefficient in blood, and the term L is assumed to be about 0.0095 cm, which represents the height of the spacer 60:

$$iss = \frac{i(5)}{1 + 4\exp\left(\frac{-4\pi^2 D \times 0.975}{L^2}\right)}$$ Eq. 4

In exemplary step 390, a first blood glucose concentration $G_1$ is determined by Equation 5 that utilizes current $i_{2(Corr)}$, (which is proportional to glucose and has a relative fraction of current removed that is ascribed to interferents):

$$G_1 = \left(\frac{|i_r|}{|i_l|}\right)^p (a|i_{2CORR}| - zgr);$$ Eq. 5 where:

$$i_r = \sum_{t=4.4}^{t=5} i(t);$$

$$i_l = \sum_{t=1.4}^{t=4} i(t);$$

$$i_{2(Corr)} = \left(\frac{|i_{pc}| + b|i_{ss}| - c|i_{pb}|}{|i_{pc}| + b|i_{ss}|}\right) i_r;$$ Eq. 5.1 and a, b, c, p, and zgr are manufacturing parameters. In the examples described herein, a is approximately 0.192, b is approximately 0.68, c is approximately 2, p is approximately 0.52, and zgr is approximately 2.

Although the applied voltages are given as positive values in the preferred embodiments, the same voltages in the negative domain could also be utilized to accomplish the intended purpose of the claimed invention.

In the exemplary embodiment, the current $i_{pb}$ was selected to be a current measured when the voltage applied to the electrodes are greater than 20 mV, and approximately 300 mV. Consequently, in the embodiment of the '899 application, the current is measured (in FIG. 7B) when the applied voltage is 300 mV (in FIG. 6A). The system thus looks for a current value for the current output $i_{pb}$ at about 1.1 seconds to ensure that the applied voltage is actually at about 300 mV.

In this exemplary embodiment, $i_{pb}$ is the current measured at approximately 1.1 second; $i_{pc}$ is current measured from the electrodes of the strip 62 at approximately 4.1 seconds; $i_{ss}$ is the current measured at approximately 5 seconds. For ease of notation, Eq. 5.1 for this known glucose concentration calculation, can be represented in the following notation as Equation 5.2:

$$i_{2(Corr)} = \left(\frac{|i_{4.1}| + b|i_5| - c|i_{1.1}|}{|i_{4.1}| + b|i_5|}\right) i_r$$ Eq. 5.2

In exemplary step 400, a corrected blood glucose concentration $G_{corr}$ is determined with the first blood glucose concentration $G_1$ and $i_{pb}$. In an embodiment, the corrected blood glucose concentration, identified here as $G_{corr1}$ is determined by Equation 6:

$$G_{corr1} = G_1 * (A + B * i_{1.1})$$ Eq. 6 where coefficients A and B are empirically derived and in the preferred embodiments, A is approximately 1.0004 and B is approximately 0.0077.

In a more preferred embodiment, the corrected blood glucose, indicated here as $G_{corr2}$ is determined by Equation 7. It should be noted herein that $G_{corr1}$ or $G_{corr2}$ may be referred to as corrected glucose concentration $G_{corr}$ and vice versa, depending on the context of whether only Equation 6 or Equation 7 is used or when both equations are used.

$$G_{corr2} = G_1 * (C + D * i_{1.1} + E * (i_{1.1})^2)$$ Eq. 7 where the coefficients C, D and E are empirically derived, and in the preferred embodiments, C is approximately 0.889; D is approximately 0.022; and E is approximately −0.00036.

In exemplary step 410, the corrected blood glucose concentration is displayed on the meter 10. Because additional interferents are taken into account, applicants have demonstrated that the corrected blood glucose concentration as being surprisingly more accurate.

Example

Determination of corrected blood glucose concentration using a linear equation and a polynomial equation to fit the data.

Data was obtained for seven lots of test strips by testing each lot with whole blood sample containing glucose at 65, 240 or 450 mg/dL, uric acid at 0-24 mg/dl and hematocrit at approximately 38% to approximately 44%. Sixteen (16) test strips at each condition of glucose, uric acid and hematocrit was tested for each lot of test strips. Test currents were also measured at 1.1 seconds, 4.1 seconds and 5 seconds and the first glucose concentration, $G_1$, was determined for each data point using Equation 5.

The corrected blood glucose concentration was then determined for each $G_1$ by using Equations 6 and 7 and test current measured at 1.1 seconds. The bias, which is an estimate of the relative error in the glucose measurement, was next calculated for each $G_1$ and for each corrected glucose concentration determined with Equations 6 and 7. The bias for each $G_1$ and each corrected glucose concentration was determined with equations of the form:

$$\text{Bias}_{abs} = G_{calculated} - G_{reference} \quad \text{Eq. 8}$$

for $G_{reference}$ less than 75 mg/dL glucose and with a bias target of 15 mg/dL or 20% and $$\text{Bias}_{\%} = \left(\frac{G_{calculated} - G_{reference}}{G_{reference}}\right) * 100 \quad \text{Eq. 9}$$

for $G_{reference}$ greater than or equal to 75 mg/dL glucose and with a bias target of 15 mg/dL or 20% where $\text{Bias}_{abs}$ is absolute bias, $\text{Bias}_{\%}$ is percent bias, $G_{calculated}$ is the uncorrected or corrected glucose concentration determined by Equations 6 and 7, and $G_{reference}$ is the reference glucose concentration.

Note that the limits for $G_{reference}$ at which Equation 8 and Equation 9 apply vary according to the bias target. For example, if the bias target is 12 mg/dL or 15%, then Equation 8 is used for $G_{reference\ less}$ than 80 mg/dL glucose and Equation 9 is used for $G_{reference}$ greater than or equal to 80 mg/dL.

The plasma uric acid concentration was then estimated using the following equation:

$$\text{Estimated Plasma UA} = \text{Donor UA} + (\text{spiked WB UA})*(100/(100-\%\text{ HCT})) \quad \text{Eq. 10}$$

where

Estimated Plasma UA is estimated plasma uric acid concentration,

Donor UA is donor uric acid concentration, spiked WB UA is uric acid concentration spiked into whole blood, and % HCT is percent hematocrit.

Figure 8A:
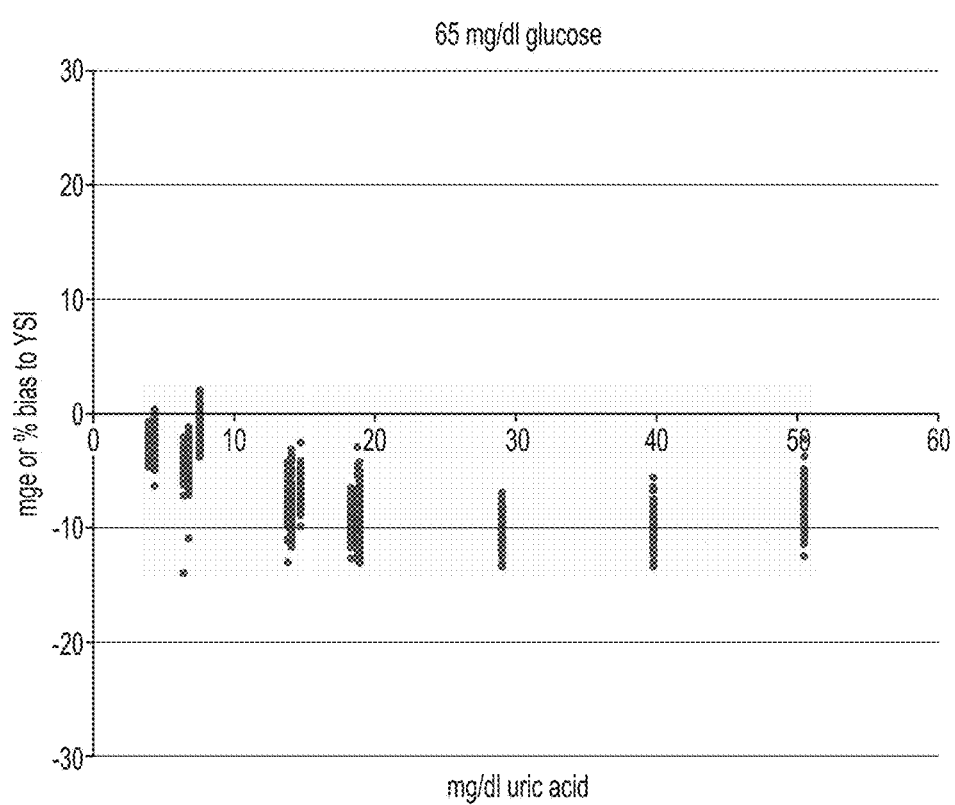
FIGS. 8A, 8B, and 8C illustrate uncompensated bias with respect to YSI reference calculated with the known glucose concentration algorithm.
Figure 8B:
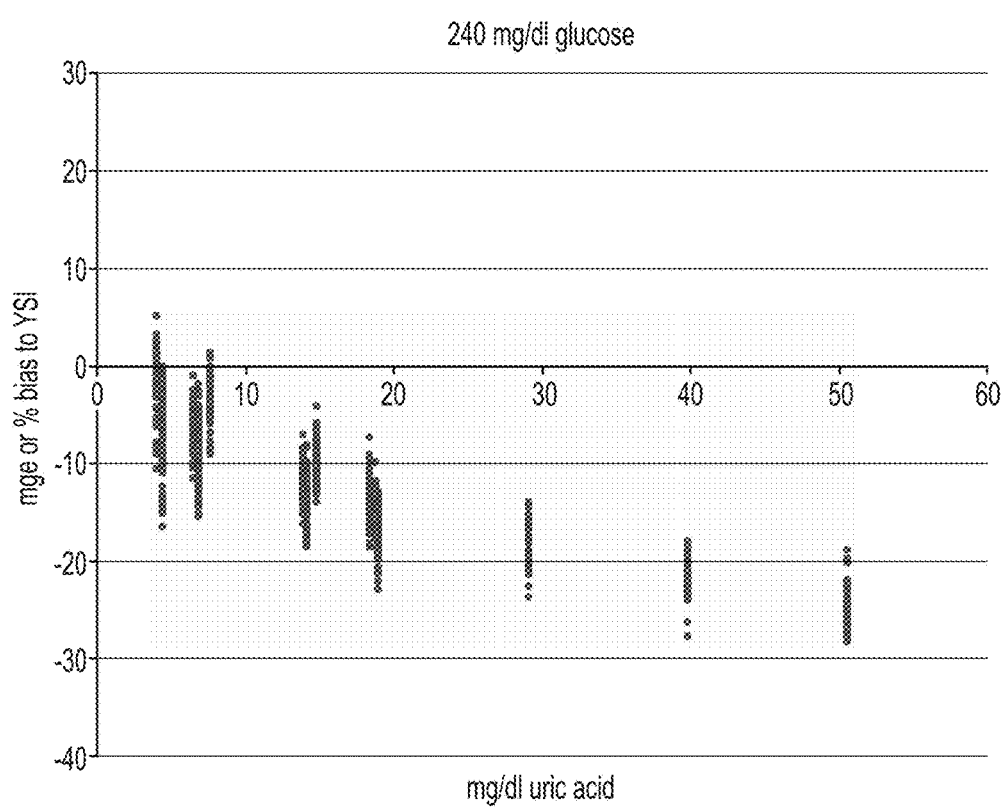
Figure 8C:
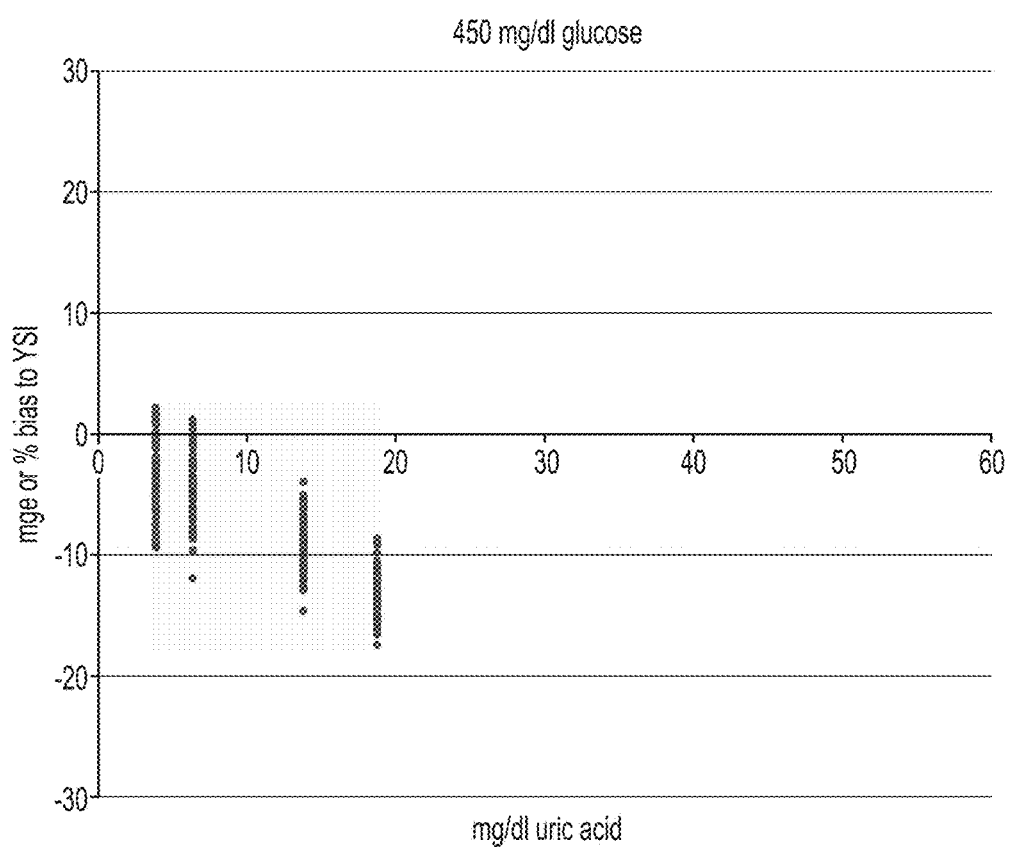
Figure 9A:
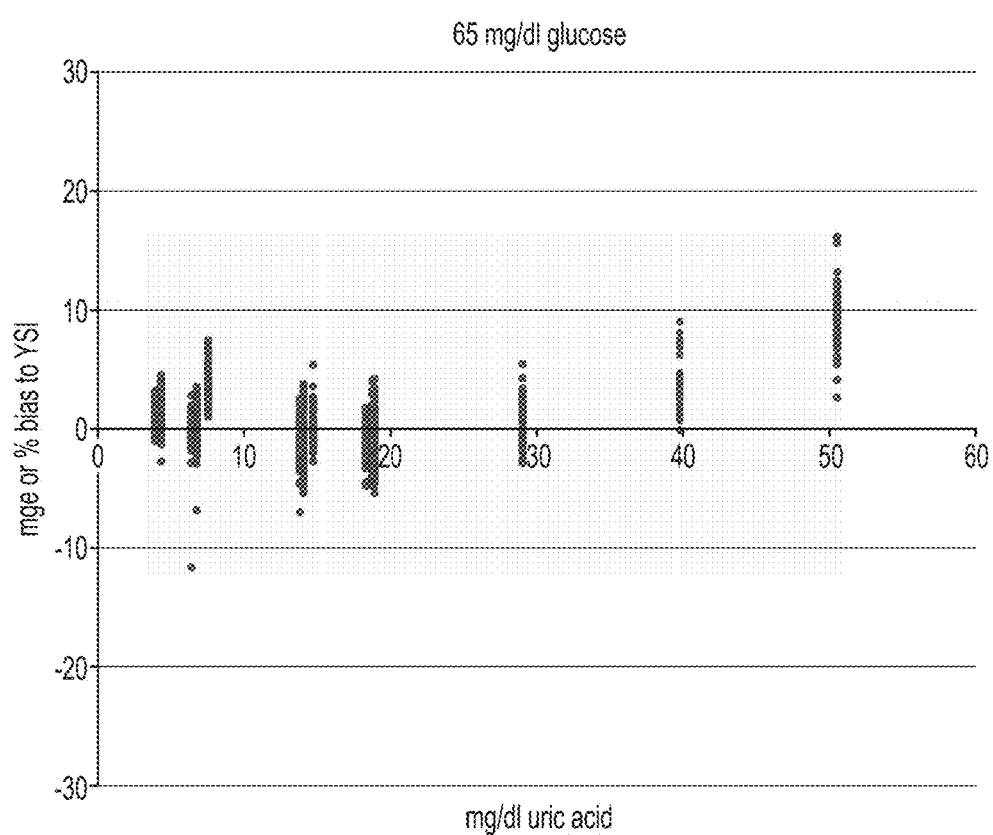
FIGS. 9A, 9B, and 9C illustrate uncompensated bias with respect to YSI reference calculated with a first exemplary glucose concentration algorithm shown and described herein.
Figure 9B:
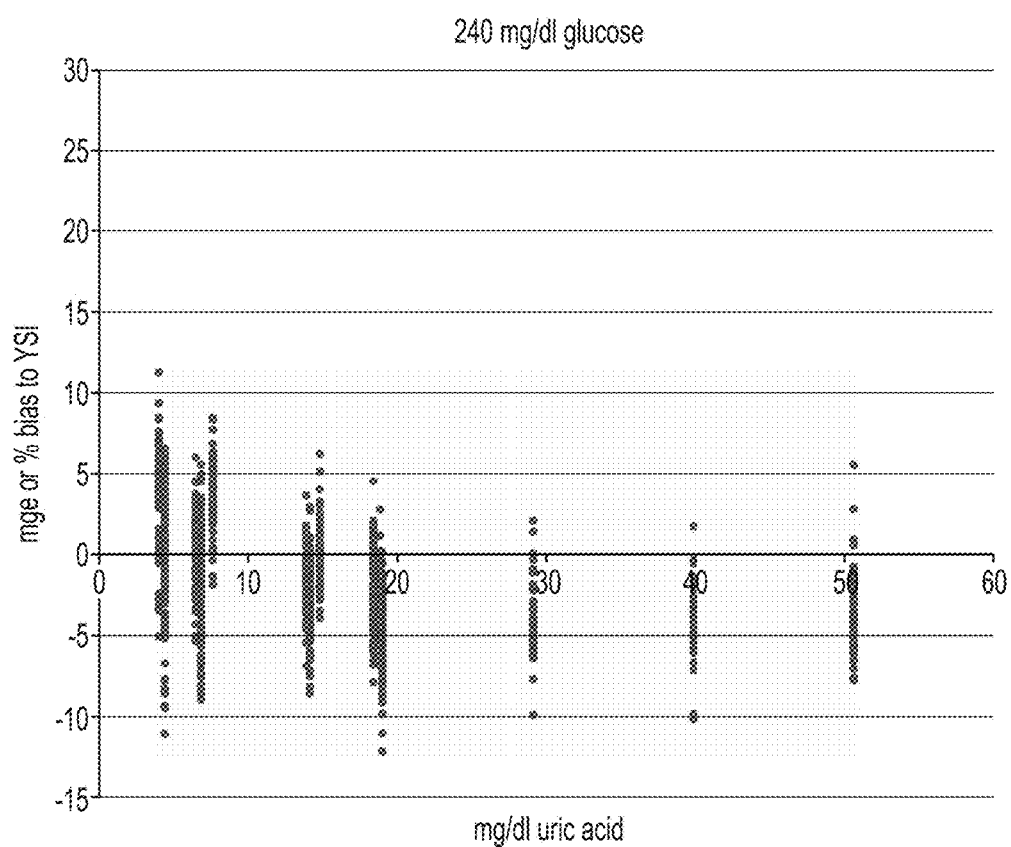
Figure 9C:
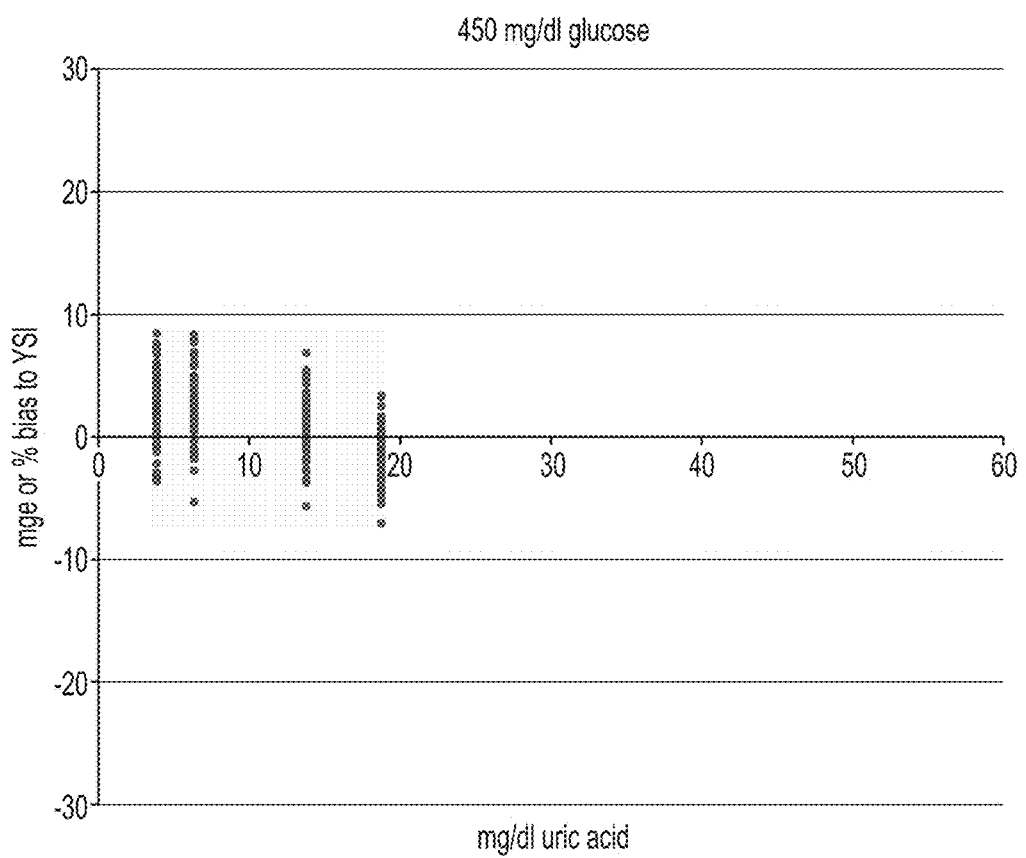
Figure 10A:
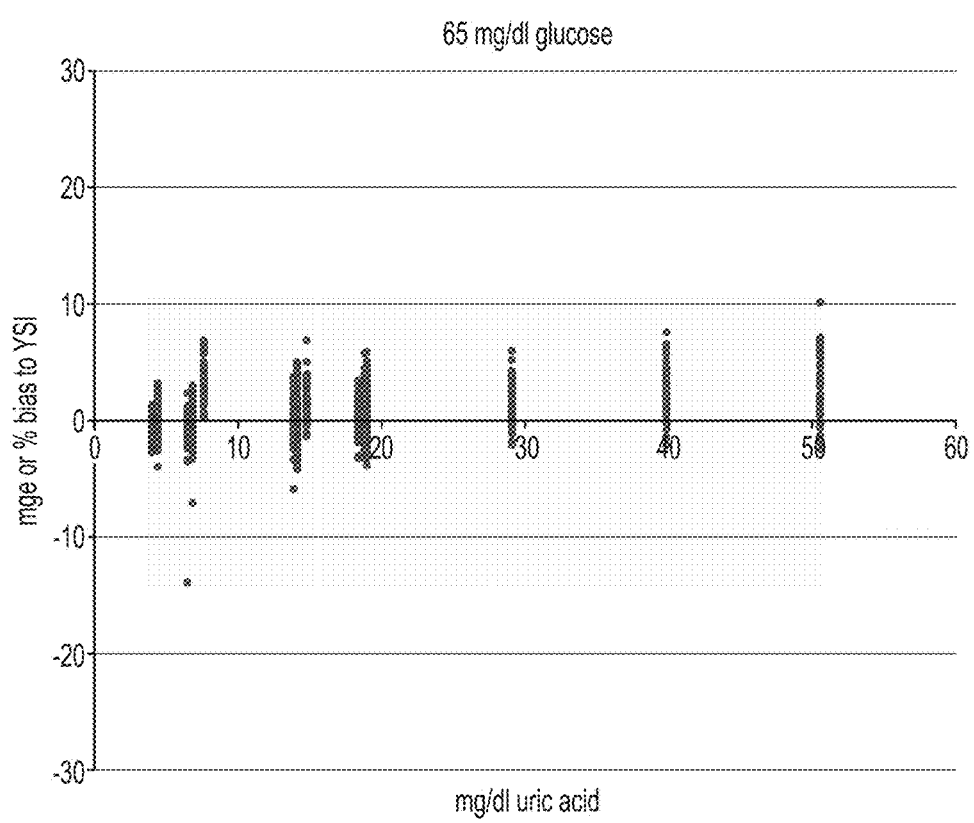
FIGS. 10A, 10B, and 10C illustrate uncompensated bias with respect to YSI reference calculated with a second exemplary glucose concentration algorithm shown and described herein.
Figure 10B:
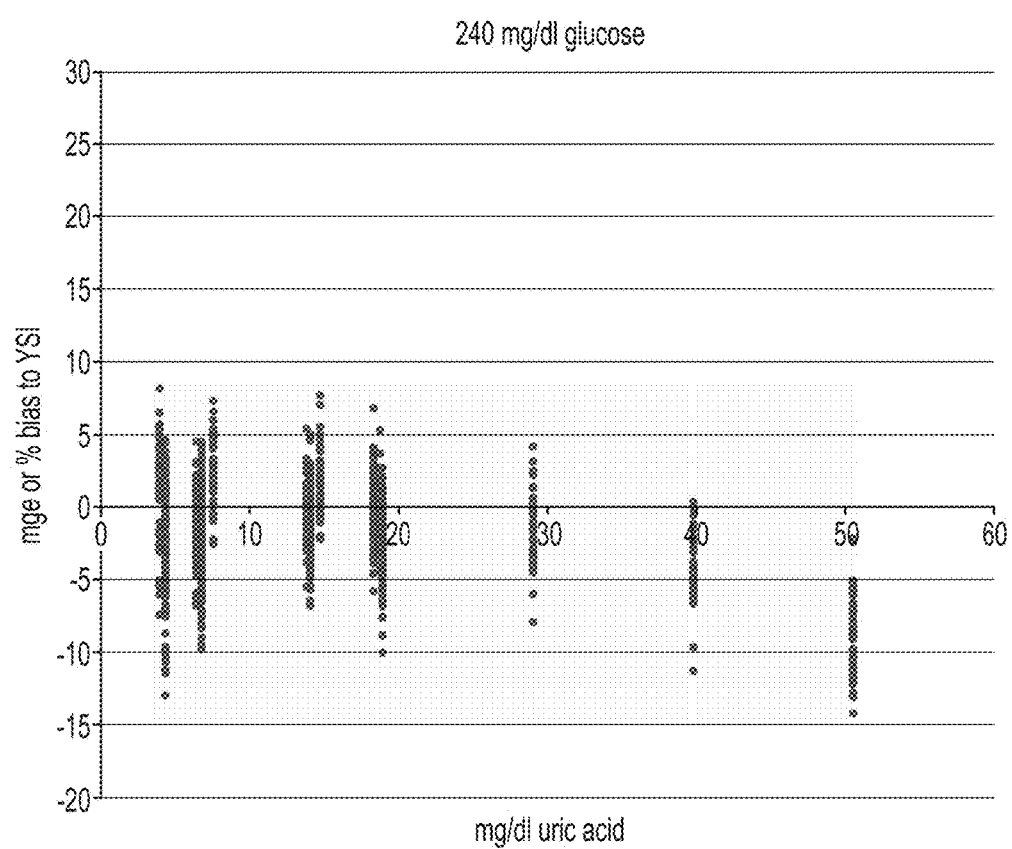
Figure 10C:
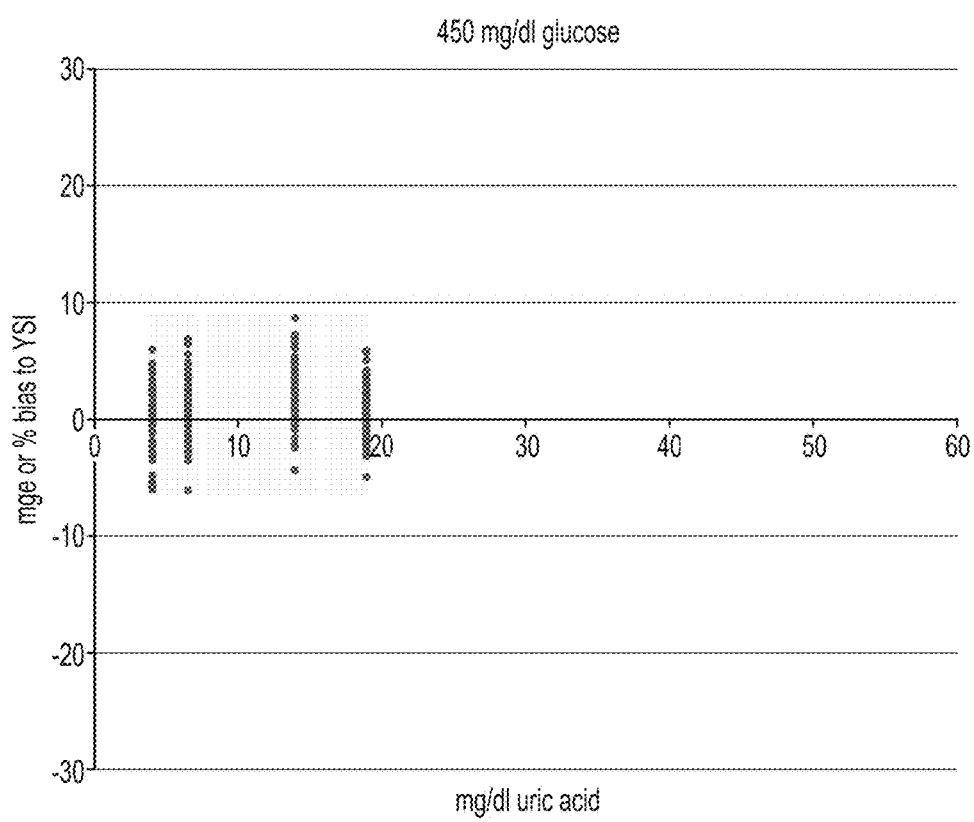

FIGS. 8A-8C, 9A-9C, and 10A-10C illustrate respective bias plots of bias versus estimated plasma uric acid concentration. FIGS. 8A, 8B, and 8C illustrate the bias plot of data as compared to YSI reference data in which the known glucose concentration calculation was used to determine the glucose concentration. FIGS. 9A, 9B, and 9C illustrate the bias plot of corrected data as compared to YSI reference data in which Equation 6 was used to determined corrected glucose concentration (i.e., a linear equation was used to determine corrected glucose concentration). FIGS. 10A, 10B, and 10C illustrate the bias plot of corrected data as compared with YSI reference data in which Equation 7 was used to determined corrected glucose concentration (i.e., a polynomial equation was used to determine corrected glucose concentration).

The data from FIGS. 8A-8C, 9A-9C, and 10A-10C may also be presented as a percentage falling within different ISO (International Standards Organization) bias criteria with respect to a YSI 2700 clinical instrument (available from YSI LifeSciences at http://www.ysilifesciences.com/index.php?page=ysi-2700-select-bioprocess-monitoring), as illustrated in Tables 1-3 below. It should be noted that the data in Tables 2 and 3 indicate an increase in the percent of data falling within each ISO bias criteria when either a linear or polynomial equation, respectively, is used to correct the glucose concentration data for uric acid interference. The results were surprising in the magnitude of the improvements of the percentage of glucose concentration values with respect to the YSI reference data across a fixed range of glucose values (e.g., at 65 mg/dL; 240 mg/dL; and at 450 mg/dL). In Tables 1-3, a total number of approximately 2469 blood glucose tests were utilized as part of the database for this invention. In particular, for the glucose thresholds 65 mg/dL there were 1107 tests; for 240 mg/dL there were 1106; and for 450 mg/dL, there were 256 tests.

TABLE 1

Summary of Bias Results for $G_1$ (uncorrected glucose concentration, i.e., from the known calculation technique) data:

| ISO Bias Criteria | Percent within Bias Criteria | | |
|---|---|---|---|
| Approx. (mg/dL or %) | 65 mg/dl glucose | 240 mg/dl glucose | 450 mg/dl glucose |
| +/−10 mg/dL or 12% | 82.4 | 49.2 | 66.4 |
| +/−12 mg/dL or 15% | 97.6 | 71.0 | 95.3 |
| +/−15 mg/dL or 20% | 100 | 90.0 | 100 |

TABLE 2

Summary of Bias Results for glucose concentration corrected with the technique associated with Equation 6

| ISO Bias Criteria | Percent within Bias Criteria | | |
|---|---|---|---|
| Approx. (mg/dL or %) | 65 mg/dl glucose | 240 mg/dl glucose | 450 mg/dl glucose |
| 10 mg/dL or 12% | 97.9 | 99.9 | 100 |
| 12 mg/dL or 15% | 99.5 | 100 | 100 |
| 15 mg/dL or 20% | 99.8 | 100 | 100 |

TABLE 3

Summary of Bias Results for glucose concentration corrected with the techniques associated with Equation 7

| ISO Bias Criteria | Percent within Bias Criteria | | |
|---|---|---|---|
| Approx. (mg/dL or %) | 65 mg/dl glucose | 240 mg/dl glucose | 450 mg/dl glucose |
| 10 mg/dL or 12% | 99.8 | 99.5 | 100 |
| 12 mg/dL or 15% | 99.9 | 100 | 100 |
| 15 mg/dL or 20% | 100 | 100 | 100 |

As shown in Table 1, at a tested concentration of 65 mg/dL of glucose concentration, the use of the known glucose concentration calculation technique resulted in the percentage of the glucose concentration data being within ±10 mg/dL of the reference YSI value of about 82%.

Table 2, on the other hand, shows that the data generated using the improved technique associated with Equation 6 as greatly improving the measured data. For example, at the tested concentration of 65 mg/dL of glucose concentration, the percent age of the glucose concentration within 10 mg/dL or 12% of the reference YSI value is about 98%, which is substantially improved from the 82.4%. It was also discovered that even greater improvement could be had when the improved technique of Equation 7 is utilized. For example, at a tested concentration of 65 mg/dL of glucose concentration in Table 3, the use of Equation 7 resulted in the percentage of the glucose concentration data being within 10 mg/dL of the reference YSI value of about 99.8% as compared to 82.4% in Table 1.

The improvements were even more significant at higher glucose concentration levels. Referring back to Table 1, at a tested concentration of 240 mg/dL of glucose concentration, the use of the known glucose concentration calculation resulted in the percentage of the glucose concentration data being within 10 mg/dL or 12% of the reference YSI value of about 49.2%. In contrast, as shown in Table 2, the percentage of glucose concentrations derived from Equation 6 is 99.9% and at the tested glucose concentration of 450 mg/dL, the percentage of results derived from Equation 6 was even greater, at 100% as compared to 80.1% in Table 1 for those glucose concentrations derived using the known calculation technique.

In conclusion, the system and methods described and illustrated herein can be used to determine a glucose concentration corrected for a reducing interferent agent such as, for example, uric acid. Thus, the glucose result obtained with the exemplary subject system and method is believed to be more accurate.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining blood glucose concentration with a glucose measurement system that includes a test strip and test meter, the test meter having a microcontroller configured to apply a plurality of test voltages comprising first, second and third test voltages to the test strip and measure a current transient output resulting from an electrochemical reaction in a test chamber of the test strip, the method comprising:

inserting the test strip into a strip port connector of the test meter to connect at least two electrodes of the test strip to a strip measurement circuit;

initiating a test sequence after deposition of a sample by causing the first test voltage to be applied, the first test voltage causing a transformation of analytes in the sample from one form to a different form;

switching a first test voltage to a second test voltage different than the first test voltage;

changing the second test voltage to a third test voltage different from the second voltage;

measuring a second current output of the current transient from the electrodes after the changing from the second test voltage to the third test voltage;

estimating a current that approximates a steady state current output of the current transient after the third test voltage is maintained at the electrodes;

calculating a blood glucose concentration based on the first, second and third current output of the current transient with an equation of the form:

$$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right) i_r$$

where:

a, b, c, p, zgr comprise manufacturing parameters;

$i_{4.1}$ comprises the current measured at about 4.1 seconds after initiation of test sequence;

$i_5$ comprises the current measured at about 5 seconds after initiation of test sequence;

$i_{1.1}$ comprises the current measured at about 1.1 seconds after initiation of test sequence; and correcting the blood glucose concentration with an equation of the form:

$$G_{corr} = G_1 * (A + B * i_{1.1})$$

where $G_{corr}$ comprises a corrected blood glucose concentration and coefficients A and B comprise empirically derived coefficients.

2. The method of claim 1, in which the coefficients A and B comprise approximately 1.004 and approximately 0.0077, respectively.

3. A method of determining blood glucose concentration with a glucose measurement system that includes a test strip and test meter, the test meter having a microcontroller configured to apply a plurality of test voltages comprising a first test voltage, a second test voltage, and a third test voltage to the test strip and measure a current transient output resulting from an electrochemical reaction in a test chamber of the test strip, the method comprising:

inserting the test strip into a strip port connector of the test meter to connect at least two electrodes of the test strip to a strip measurement circuit;

initiating a test sequence after deposition of a sample by applying the first test voltage;

causing a transformation of analytes in the sample from one form to a different form;

switching the first test voltage to a second test voltage different than the first test voltage;

changing the second test voltage to a third test voltage different from the second voltage;

measuring a second current output of the current transient from the electrodes after the changing from the second test voltage to the third test voltage;

estimating approximate steady state current output of the current transient after the third test voltage is maintained at the electrodes;

calculating a blood glucose concentration based on the first, second and third current output of the current transient with an equation of the form:

$$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right)i_r$$

where:
a, b, c, p, zgr comprise manufacturing parameters;
$i_{4.1}$ comprises the current measured at about 4.1 seconds after initiation of test sequence;
$i_5$ comprises the current measured at about 5 seconds after initiation of test sequence;
$i_{1.1}$ comprises the current measured at about 1.1 seconds after initiation of test sequence; and
correcting the blood glucose concentration with an equation of the form:

$$G_{corr} = G_1 * (C + D * i_{1.1} + E * (i_{1.1})^2)$$

where $G_{corr}$ comprises a corrected blood glucose concentration and coefficients C, D and E comprise empirically derived coefficients.

4. The method of claim 3, in which the step of switching comprises changing the polarity of the second test voltage with respect to the first test voltage.

5. The method of claim 3, in which the deriving of the first corrected glucose concentration comprises calculating with equations of the form:

$$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right)i_r$$

where:
a, b, c, p, zgr comprise manufacturing parameters;
$i_{4.1}$ comprises the current measured at about 4.1 seconds after initiation of test sequence;
$i_5$ comprises the current measured at about 5 seconds after initiation of test sequence;
$i_{1.1}$ comprises the current measured at about 1.1 seconds after initiation of test sequence; and $$G_{corr1} = G_1 * (A + B * i_{1.1})$$

where $G_{corr1}$ comprises a first corrected blood glucose concentration and coefficients A and B comprise empirically derived coefficients.

6. The method of claim 3, in which the deriving of the second corrected glucose concentration comprises calculating with equations of the form $$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right)i_r$$

where:
a, b, c, p, zgr comprise manufacturing parameters;
$i_{4.1}$ comprises the current measured at about 4.1 seconds after initiation of test sequence;
$i_5$ comprises the current measured at about 5 seconds after initiation of test sequence;
$i_{1.1}$ comprises the current measured at about 1.1 seconds after initiation of test sequence; and
correcting the blood glucose concentration with an equation of the form:

$$G_{corr2} = G_1 * (C + D * i_{1.1} + E * (i_{1.1})^2)$$

where $G_{corr2}$ comprises a corrected blood glucose concentration and coefficients C, D and E comprise empirically derived coefficients.

7. The method of claim 3, in which the measuring of the first current output comprises measuring a current output of the at least two electrodes at about 1.1 seconds after initiation of test sequence.

8. The method of claim 3, in which the measuring of the second current output comprises measuring a current output of the at least two electrodes at about 4.1 seconds after initiation of test sequence.

9. The method of claim 3, in which the estimating of the steady state current output comprises measuring a current output of the at least two electrodes at about 5 seconds after initiation of test sequence.

10. The method of claim 3, in which the coefficients A, B, C, D, and E comprise approximately 1.004, approximately 0.0077, approximately 0.889, approximately 0.0220 and approximately −0.00036, respectively.

11. The method of claim 5, in which the coefficients A and B comprise approximately 1.004 and approximately 0.0077, respectively.

12. The method of claim 5, in which the coefficients C, D, and E comprise approximately 0.889, approximately 0.0220 and approximately −0.00036, respectively.

13. The method of claim 5, in which the manufacturing parameter a comprises approximately 0.192, b comprises approximately 0.68, c comprises approximately 2, p comprises approximately 0.52, and zgr comprises approximately 2.

14. The method of claim 3, in which the threshold percentage is greater than 10% difference in glucose concentrations.

15. A blood glucose measurement system comprising:
an analyte test strip including:
a substrate having a reagent disposed thereon;
at least two electrodes proximate the reagent in test chamber;

an analyte meter including:
  a strip port connector disposed to connect to the two electrodes;
  a power supply; and
  a microcontroller electrically coupled to the strip port connector and the power supply, the microcontroller programmed to,
  apply a first test voltage;
  switch the first test voltage to a second test voltage different than the first test voltage;
  change the second test voltage to a third test voltage different from the second test voltage,
  measure a second current output of the current transient from the electrodes after the change from the second test voltage to the third test voltage,
  estimate a current that approximates a steady state current output of the current transient after the third test voltage is maintained at the electrodes, and
  determine a glucose concentration $G_1$ and a corrected glucose concentration $G_{corr}$ to account for interfering agents so that at least 97% of corrected test results are within respective bias criterion of ±10 mg/dL at 65 mg/dL, 240 mg/dL, or at 450 mg/dL as compared to reference YSI data; ±12 mg/dL at 65 mg/dL, 240 mg/dL, or 450 mg/dL as compared to reference YSI data; and ±15 mg/dL at 65 mg/dL, 240 mg/dL, or 450 mg/dL as compared to reference YSI data, the glucose concentration and the corrected glucose concentration based on the first, second and third current output and being derived from the following equations:

$$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right)i_r$$

where:
  a, b, c, p, zgr comprise manufacturing parameters;
  $i_{4.1}$ comprises the current measured at about 4.1 seconds after initiation of test sequence;
  $i_5$ comprises the current measured at about 5 seconds after initiation of test sequence;
  $i_{1.1}$ comprises the current measured at about 1.1 seconds after initiation of test sequence; and $$G_{corr} = G_1 * (C + D * i_{1.1} + E * (i_{1.1})^2)$$

where $G_{corr}$ comprises a corrected blood glucose concentration and coefficients C, D and E comprise empirically derived coefficients.

16. The system of claim 15, in which the manufacturing parameters a, b, c, p, zgr are such that a comprises approximately 0.192, b comprises approximately 0.68, c comprises approximately 2, p comprises approximately 0.52 and zgr comprises approximately 2.

17. The system of claim 15, in which the coefficients C, D, and E comprise approximately 0.889, approximately 0.0220 and approximately −0.00036, respectively.

* * * * *